(12) United States Patent
Sarphati et al.

(10) Patent No.: US 10,022,464 B2
(45) Date of Patent: Jul. 17, 2018

(54) STERILIZATION TRAY

(71) Applicant: ZUNO MEDICAL INC., San Jose, CA (US)

(72) Inventors: Joffrey Sarphati, San Jose, CA (US); Ryan Dean, Superior, CO (US); Michael Olmes, San Jose, CA (US)

(73) Assignee: Zuno Medical Inc., Los Gatos, CA (US)

( * ) Notice: Subject to any disclaimer, the term of this patent is extended or adjusted under 35 U.S.C. 154(b) by 18 days.

(21) Appl. No.: 14/909,387

(22) PCT Filed: Aug. 1, 2014

(86) PCT No.: PCT/US2014/049480
§ 371 (c)(1),
(2) Date: Feb. 1, 2016

(87) PCT Pub. No.: WO2015/017828
PCT Pub. Date: Feb. 5, 2015

(65) Prior Publication Data
US 2016/0193374 A1 Jul. 7, 2016

Related U.S. Application Data

(60) Provisional application No. 61/861,871, filed on Aug. 2, 2013.

(51) Int. Cl.
*A61L 2/24* (2006.01)
*A61L 2/07* (2006.01)
*A61L 2/26* (2006.01)

(52) U.S. Cl.
CPC ............ *A61L 2/24* (2013.01); *A61L 2/07* (2013.01); *A61L 2/26* (2013.01); *A61L 2202/182* (2013.01)

(58) Field of Classification Search
CPC ...... A61L 2/24; A61L 2/04; A61L 2/06; A61L 2/07; A61L 2/26; A61L 2202/12;
(Continued)

(56) References Cited

U.S. PATENT DOCUMENTS

| 4,022,324 A | 5/1977 | Schuster et al. |
| 4,105,407 A | 8/1978 | Sanderson et al. |

(Continued)

FOREIGN PATENT DOCUMENTS

| CN | 202761746 | 3/2013 |
| JP | 2001192014 | 7/2001 |

(Continued)

OTHER PUBLICATIONS

PCT/US2014/049480, "International Preliminary Report on Patentability," dated Feb. 11, 2016, 8 pages.
(Continued)

*Primary Examiner* — Timothy C Cleveland
(74) *Attorney, Agent, or Firm* — Kilpatrick Townsend & Stockton LLP

(57) ABSTRACT

An apparatus for sterilizing items and storing the sterilized items prior to use includes a container configured to receive items to be sterilized, a trap door coupled with the container, and a mechanism operatively coupled with the trap door and the container. The trap door is reconfigurable between an open configuration providing a fluid passage into the apparatus and a closed configuration in which the items are hermetically sealed within the apparatus. The mechanism is configured for selective reconfiguration of the trap door from the closed configuration to the open configuration and to automatically reconfigure the trap door from the open configuration to the closed configuration after completion of a sterilization of items disposed within the apparatus.

12 Claims, 10 Drawing Sheets

(58) Field of Classification Search
CPC ......... A61L 2202/121; A61L 2202/122; A61L 2202/14; A61L 2202/182; A61L 2202/24
See application file for complete search history.

(56) References Cited

U.S. PATENT DOCUMENTS

| | | | |
|---|---|---|---|
| 4,124,141 A | 11/1978 | Armentrout et al. | |
| 4,149,650 A | 4/1979 | Sanderson et al. | |
| 4,196,166 A | 4/1980 | Sanderson et al. | |
| 4,228,914 A | 10/1980 | Sanderson et al. | |
| 4,247,517 A | 1/1981 | Whelchel et al. | |
| 4,251,482 A | 2/1981 | Whelchel et al. | |
| D264,503 S | 5/1982 | Sanderson et al. | |
| 4,349,118 A | 9/1982 | Sanderson et al. | |
| 4,372,921 A | 2/1983 | Sanderson et al. | |
| 4,374,570 A | 2/1983 | Whelchel et al. | |
| D268,867 S | 5/1983 | Sanderson et al. | |
| 4,416,417 A | 11/1983 | Whelchel et al. | |
| 4,457,327 A | 7/1984 | Pepper et al. | |
| D275,229 S | 8/1984 | Sanderson et al. | |
| 4,466,552 A | 8/1984 | Butterworth et al. | |
| 4,482,053 A | 11/1984 | Alpern et al. | |
| 4,558,632 A | 12/1985 | Whelchel et al. | |
| 4,583,643 A | 4/1986 | Sanderson et al. | |
| 4,584,182 A | 4/1986 | Sanderson et al. | |
| 4,612,872 A | 9/1986 | Sanderson et al. | |
| 4,716,025 A | 12/1987 | Nichols et al. | |
| 4,748,003 A | 5/1988 | Riley et al. | |
| 4,754,595 A | 7/1988 | Sanderson et al. | |
| 4,774,063 A | 9/1988 | Runnells et al. | |
| 4,915,913 A | 4/1990 | Williams et al. | |
| 5,223,229 A | 6/1993 | Brucker et al. | |
| 5,277,876 A | 1/1994 | Wagner et al. | |
| 5,352,416 A | 10/1994 | Wagner | |
| 5,368,821 A | 11/1994 | Schmoegner et al. | |
| 5,590,778 A | 1/1997 | Dutchik et al. | |
| 6,837,027 B2 | 1/2005 | Hickey et al. | |
| 7,132,089 B2 * | 11/2006 | Lacabanne | A61L 2/24 206/363 |
| 7,942,264 B2 | 5/2011 | Friderich et al. | |
| 8,006,982 B2 | 8/2011 | Whitlow et al. | |
| 8,327,606 B2 | 12/2012 | Kemp et al. | |
| 9,057,657 B2 | 6/2015 | Heckenberger et al. | |
| 2012/0082589 A1 | 4/2012 | Ladison et al. | |
| 2012/0156096 A1 | 6/2012 | Allen et al. | |
| 2012/0189508 A1 | 7/2012 | Kreidler | |
| 2013/0280134 A1 | 10/2013 | Hoffman et al. | |
| 2014/0056759 A1 | 2/2014 | Jacene et al. | |
| 2015/0374868 A1 | 12/2015 | Chemlar et al. | |

FOREIGN PATENT DOCUMENTS

| | | |
|---|---|---|
| JP | 2008184203 | 8/2008 |
| WO | 2015017828 | 2/2015 |

OTHER PUBLICATIONS

PCT/US2014/049480, "International Search Report and Written Opinion," dated Nov. 5, 2014, 10 pages.

* cited by examiner

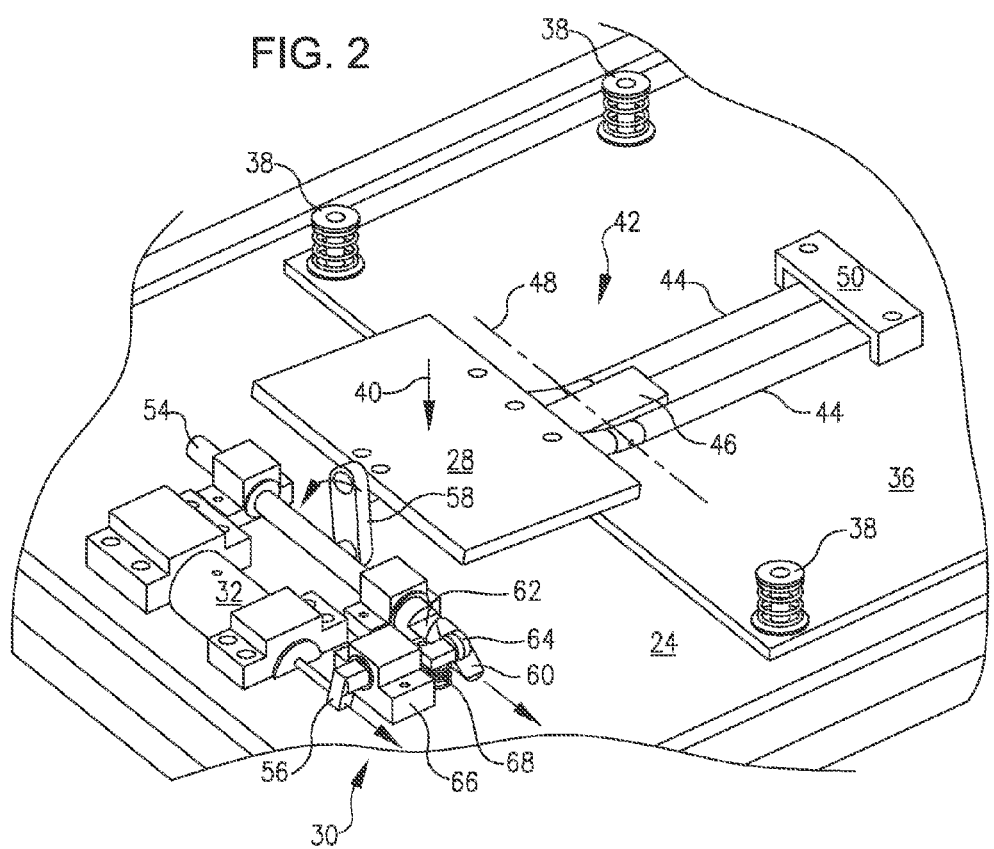

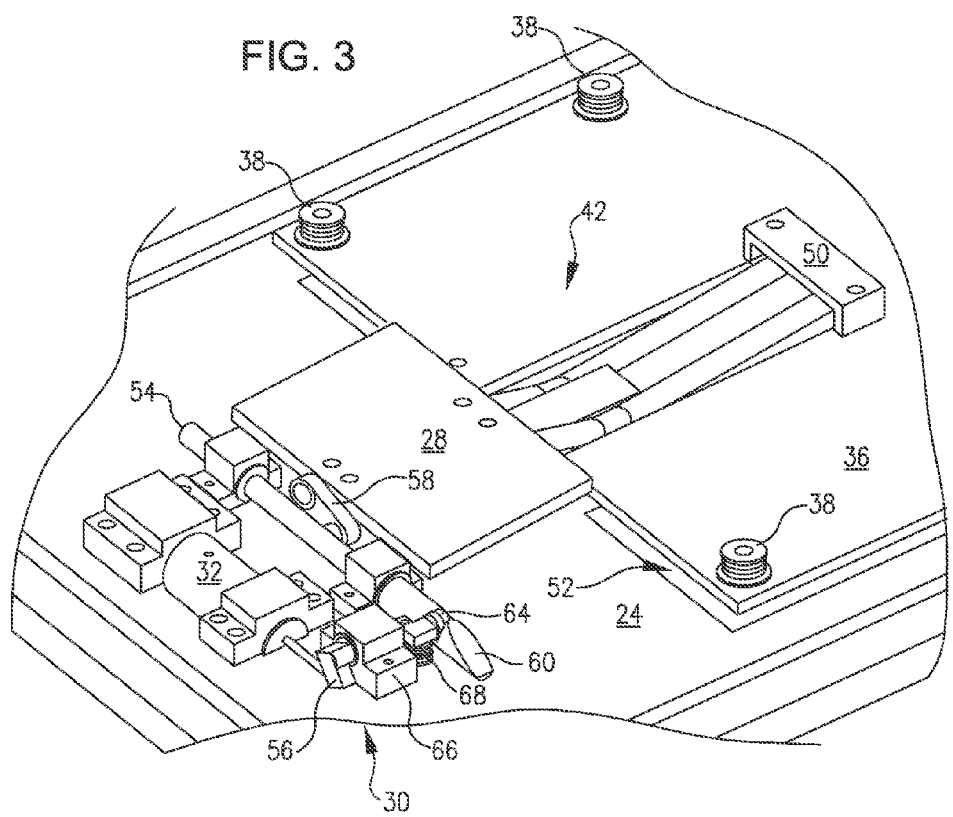

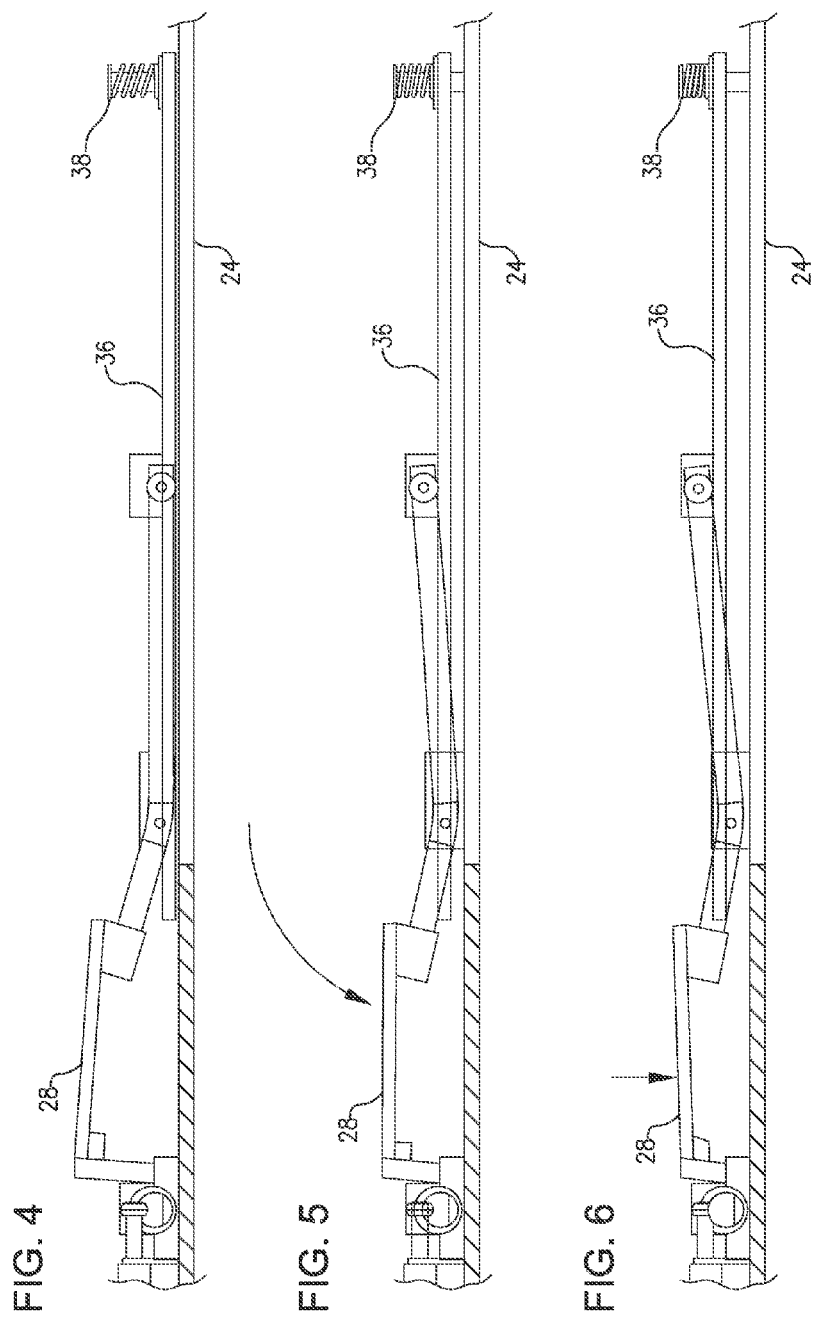

STERILIZATION TRAY

CROSS-REFERENCES TO RELATED APPLICATIONS

This application is the U.S. national stage of PCT/US2014/049480, filed Aug. 1, 2014, which claims the benefit of priority to U.S. Provisional Application No. 61/861,871, filed Aug. 2, 2013, the disclosures of both of which are incorporated herein by reference in their entirety.

BACKGROUND

Sterilization of items is used in various industries, including health care, pharmaceutical, and food processing industries. A common and proven method used for sterilization applies pressurized high temperature steam in a pressure chamber or vessel for a prescribed period of time. Pressurized high temperature steam within a stainless steel pressure chamber is used for sterilization of laboratory equipment and in the industrial manufacturing sector.

In hospital and health care environments, laboratory environments, and in the pharmaceutical and food processing industry, sterilization may be accomplished by contacting the item to be sterilized with high temperature steam within a pressure vessel. Alternatively, the item to be sterilized can be contacted with a low temperature sterilizing medium (e.g., ethylene oxide or equivalent low temperature sterilizing medium) in a pressure vessel. Various types of sterilization pressure vessels and autoclave chambers can be used utilized to sterilize items. In many instances, the sterilizing medium is contacted with item being sterilized.

At the end of a sterilization cycle, items inside the sterilization chamber are sterile. Unfortunately, the air in the room where the sterilization chamber is installed will typically contain dust particles, which may carry micro-organisms. Accordingly, sterilized items taken out of a sterilization chamber may become contaminated. Additionally, sterilized items may be stored for a period of time before use. Moreover, in a hospital setting, sterilized items will typically be transported through the hospital to where they are used. Accordingly, sterilized items, when not protected, may be re-contaminated prior to use.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Apparatus and related methods are provided for sterilizing items (e.g., surgical instruments, instrument trays, implants, and/or implant trays) within a sterilization chamber and subsequent storage thereof until use. An example apparatus includes a container having an internal volume into which items to be sterilized are placed. The apparatus is configurable into an open configuration in which the internal volume is in fluid communication with the surrounding environment. The apparatus (and the items to be sterilized therein) is placed into a sterilization chamber (e.g., an autoclave). The apparatus is configured to automatically reconfigure into a closed configuration in which the internal volume is hermetically isolated from the surrounding environment after the completion of a sterilization of items within the apparatus. The sterilization of the items can be accomplished using any suitable approach, for example, the temperature inside the apparatus can be greater than a selected sterilization temperature for at least a predetermined amount of time. The apparatus can remain in the closed configuration until when the sterilized items are used, thereby preventing recontamination of the sterilized items prior to use. The apparatus can be reused for sterilizing additional batches of items, thereby providing an effective and economical means to sterilize items and store the sterilized items prior to use.

The apparatus disclosed herein can be used for the sterile processing of instrumentation in a hospital. Instrument trays can be placed into a base portion and a sterilization lid attached to the base portion. A user can press down on an actuation member on the sterilization lid to open a trap door to allow surrounding air to enter into the apparatus. The trap door is held open by a latch mechanism. The apparatus can then be placed into a sterilization chamber (e.g., an autoclave). Once the temperature in the sterilization chamber reaches a certain point (e.g., as detected by an electronic temperature sensor), a timer is started. After a predetermined amount of time has elapsed, as tracked by the timer, the mechanism releases the trap door, thereby sealing the apparatus. The trap door can be closed after ample time has passed to ensure sterilization of the items within the apparatus. Closing the trap door hermetically isolates the sterilized items from the outside world. The apparatus can remain sealed until the sterilized items are accessed for use in an operating room.

Thus, in one aspect, an apparatus is provided for sterilizing surgical implements within a sterilization chamber and storing the sterilized surgical implements prior to use. The apparatus includes a container configured to receive one or more surgical implements, a trap door coupled with the container, and a mechanism operatively coupled with the trap door and the container. The trap door is coupled with the container so as to be reconfigurable between a closed configuration and an open configuration. In the closed configuration, the trap door and the container at least partially define an internal volume that is hermetically sealed. In the open configuration, the trap door is displaced from the container to form a fluid passage between the internal volume and a volume within the sterilization chamber that is external to the container. The mechanism is configured for selective reconfiguration of the trap door from the closed configuration to the open configuration. The mechanism is configured to automatically reconfigure the trap door from the open configuration to the closed configuration after completion of a sterilization of one or more surgical implements disposed within the internal volume.

In many embodiments, the container includes a base portion and a top cover that is attachable to and detachable from the base portion. One or more surgical implements can be placed into the base portion and then the top cover attached. The top cover can have an opening that is blocked by the trap door when the trap door is in the closed configuration. When in the open configuration, the trap door does not block the opening, thereby placing the internal volume of the container in fluid communication with the surrounding environment.

In many embodiments, the apparatus includes one or more spring elements that generate an interface force between the trap door and the top cover when the trap door is in the closed configuration. Such an interface force can ensure compression of an interface seal disposed between the trap door and the top cover, thereby serving to increase the effectiveness of the interface seal. In many embodiments, the one or more spring elements generate a force on the trap door that is reacted by the mechanism when the trap door is in the open configuration.

In many embodiments, the mechanism includes an actuation member and a latch device. The actuation member is configured to be manually displaced by a user to reconfigure the trap door from the closed configuration to the open configuration. The latch device is configured to maintain the trap door in the open configuration until after completion of the sterilization of the items within the apparatus.

In many embodiments, the mechanism includes a temperature sensor, a solenoid, and a control unit. The temperature sensor can be configured to generate a temperature sensor output indicative of a temperature of the internal volume. The solenoid can be coupled with the latch device and operable to unlatch the latch device so as to cause reconfiguration of the trap door from the open configuration to the closed configuration. The control unit can be configured to receive the temperature sensor output and control the solenoid. The control unit can be configured to determine when the sterilization of the items within the apparatus is complete and actuate the solenoid after the completion of the sterilization of the items to unlatch the latch device, thereby causing the apparatus to reconfigure into the closed configuration. The control unit can be configured to delay actuation of the solenoid for a period of time after completion of the sterilization.

Any suitable sterilization approach can be used. For example, the control unit can determine completion of the sterilization of the items based on the temperature of the internal volume being equal to or greater than a selected sterilization temperature for a suitable period of time.

Any suitable latch device can be used. For example, the latch device can include a rotatable link that is rotatable by the solenoid from a latched orientation that maintains the trap door in the open configuration to an unlatched orientation that permits reconfiguration of the trap door from the open configuration to the closed configuration.

The trap door can be coupled with the container using any suitable means. For example, the trap door can include a plurality of apertures with each of the apertures being configured to receive and interface with a respective guide feature attached to the container so as to constrain movement of the trap door relative to the container between the closed configuration and the open configuration.

The trap door can be coupled with the actuation member using any suitable means. For example, the actuation member can be coupled with the trap door via a beam member mounted to rotate about a pivot point that is fixed relative to the container. The pivot point can be disposed between the trap door and the actuation member so that pressing the actuation member towards the container causes the trap door to be moved away from the container.

The actuation member can be coupled with the latch device so that movement of the actuation member can be used to engage the latch device. For example, the actuation member can be coupled with the latch device via a two-force link that is oriented transverse to a movement direction of the actuation member relative to the container for each of the open and closed configurations of the trap door.

Any suitable configuration of the latch device can be used. For example, the latch device can include a latch link constrained to linear translation relative to the container. The latch link can be driven via the two-force link between a latched position used to hold the trap door in the open configuration and a position for which the trap door is in the closed configuration. The latch link can have a cam surface and a recess. Movement of the latch link toward the latched position can result in engagement between a spring-biased latch member and the cam surface to position the latch member for engagement with the recess. Actuation of the solenoid can be used to drive the spring-biased latch member out of engagement with the recess, thereby permitting movement of the latch link from the latched position to the position for which the trap door is in the closed configuration.

In many embodiments, the latch device is operatively coupled with the trap door via a linkage. The linkage transfers the force generated on the trap door by one or more spring elements into the latch device when the trap door is in the open configuration.

The mechanism can employ mechanical components instead of electrical components. For example, the mechanism can include a mechanical thermostat and a mechanical timer. The mechanical thermostat can have a first configuration at a first temperature below a sterilization temperature and a second configuration at a second temperature equal to or greater than the sterilization temperature. A latch device can be operatively coupled with the mechanical thermostat and configured to block a timing operation of the mechanical timer when the mechanical thermostat is in the first configuration and permit the timing operation when the thermostat is in the second configuration. The mechanical timer can be coupled with the trap door via a linkage so as to maintain the trap door displaced from the container until expiration of a time period determined by the mechanical timer. For example, a user displacement of the actuation member can be used to translate a geared rack to engage and rotate a timer gear drivingly coupled with the mechanical timer so as to wind the mechanical timer to enable the mechanical timer to effect the timing operation. At the end of the timed period, the geared rack can become disengaged from the timer gear to permit reconfiguration of the trap door into the closed configuration.

For a fuller understanding of the nature and advantages of the present invention, reference should be made to the ensuing detailed description and accompanying drawing

BRIEF DESCRIPTION OF THE DRAWINGS

FIGS. 2 and 3 illustrate an actuation sequence of a mechanism portion of the apparatus of FIG. 1 between a closed configuration and an open configuration.

FIGS. 4, 5, and 6 are side views of the apparatus of FIG. 1 illustrating reconfiguration of a trap door between the closed configuration and the open configuration.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Apparatus and related methods are described for sterilizing items (e.g., surgical instruments, instrument trays, implants, and/or implant trays) within a sterilization chamber and subsequent storage of the sterilized items prior to use. For example, a filter-less, reusable sterilization apparatus is described that in an initial configuration (open configuration) provides an unobstructed pathway to allow the flux of gases (e.g., air, water vapor, etc.) into and out of the apparatus. The apparatus includes a temperature-sensing component and a timer, which work together to initiate a reconfiguration of the apparatus to a closed configuration in which the apparatus is hermetically sealed. In many embodiments, the temperature-sensing component monitors temperature of the gases surrounding and/or within the apparatus until a target temperature is reached (e.g., a selected sterilization temperature for sterilizing items within the apparatus). Once the target temperature is reached, a timer is started to delay reconfiguration of the apparatus to the closed configuration for a target period of time (e.g., a duration of time required to sterilize items within the apparatus, and optionally an additional duration of time to achieve desirable environmental conditions within the apparatus). Once the target time has passed, the timer triggers reconfiguration of the apparatus into the closed configuration, thereby disrupting the gas pathway and stopping the flux of gases into or out of the apparatus. The apparatus can be kept in the closed configuration and will maintain the environment established within the apparatus at the time the reconfiguration of the apparatus and disruption of the gas pathway (e.g., a sub-atmospheric pressure state) through a hermetic seal until the contents of the apparatus are accessed for use. When access to the contents of the apparatus is required, the apparatus may either be restored to its initial (open) configuration, which will allow access to the contents directly through the unobstructed pathway described above, or the apparatus may be put into a third configuration to provide access (e.g., the apparatus's lid is removed).

Figure 1:
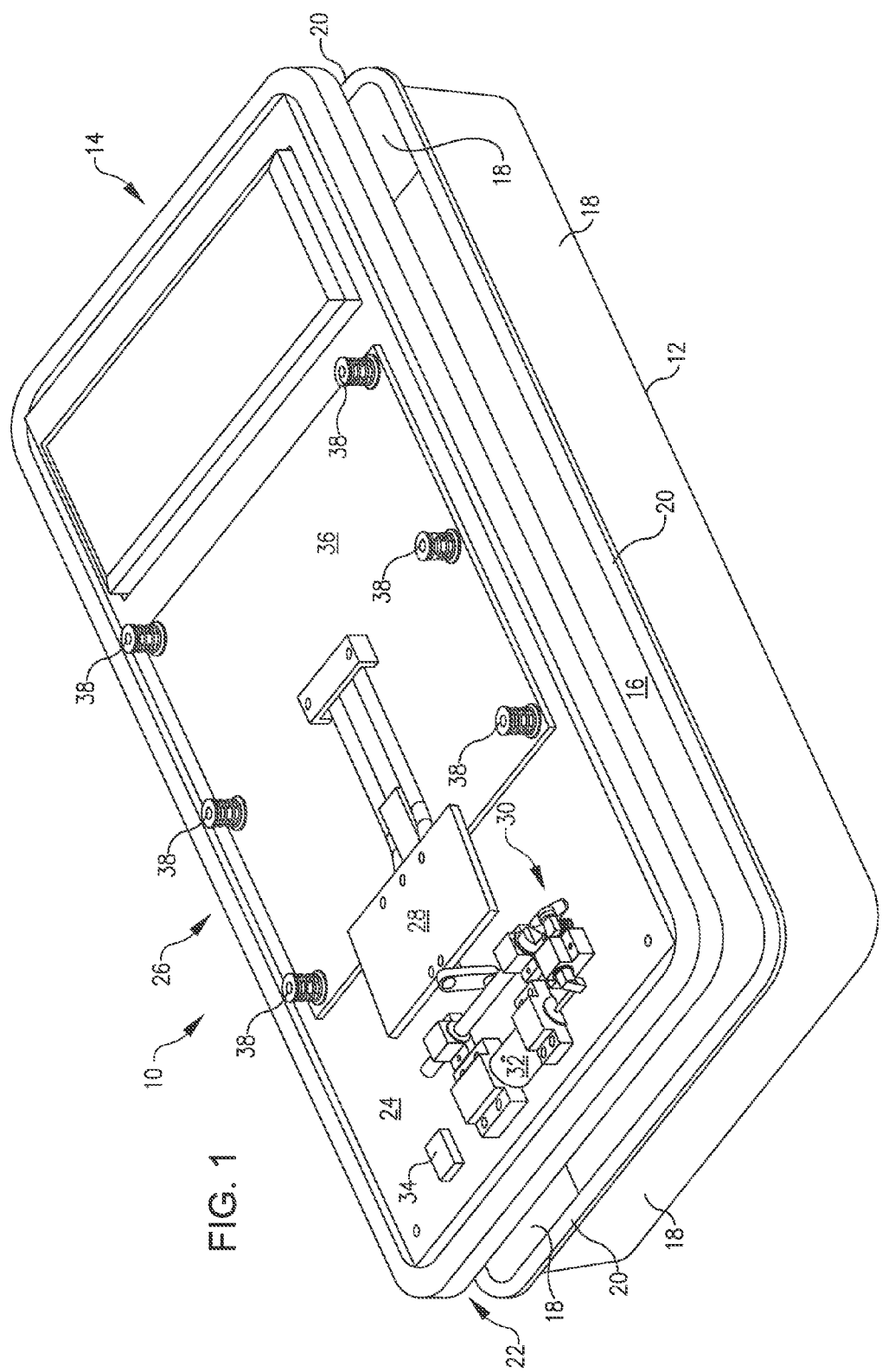
FIG. 1 illustrates an apparatus for use in sterilizing items and storing the sterilized items therein prior to use, in accordance with many embodiments.

Referring now to the drawings, in which like reference numerals represent like parts throughout the several views, FIG. 1 shows an apparatus 10 for use in sterilizing items and storing the sterilized items therein prior to use, in accordance with many embodiments. The apparatus 10 includes a base portion 12 and a top cover assembly 14.

The base portion 12 is configured to receive and hold items to be sterilized. In the illustrated embodiment, the base portion 12 has a lower surface 16 and four side walls 18. The lower surface 16 and the four side walls 18 form a fluid-tight open-ended container having an circumferential upper edge 20. The upper edge 20 is configured to sealingly interface with the top cover assembly 14, thereby defining an internal volume that can be hermetically sealed to store sterilized items prior to use.

The top cover assembly 14 is attachable to and detachable from the base portion 12. In many embodiments, the top cover assembly 14 includes a perimeter seal 22 configured to sealingly interface with the upper edge 20 of the base portion 12. In use, items to be sterilized can be placed into the base portion 12 prior to attachment of the top cover assembly 14 to the base portion 12.

The top cover assembly 14 includes a top cover base 24, a trap door assembly 26, an actuation member 28, a latch device 30, a solenoid 32, and a control unit 34. The top cover base 24 provides a base that supports the perimeter seal 22, the trap door assembly 26, the latch device 30, the solenoid 32, and the control unit 34. FIG. 1 shows the apparatus in a closed configuration in which the top cover base 24 and the trap door assembly 26 form a hermetically sealed barrier, which when coupled with the base portion 12 form a hermetically sealed internal volume for storing sterilized items prior to use.

The trap door assembly 26 includes a trap door 36 and spring-loaded mounts 38 by which the trap door 36 is coupled with the top cover base 24. Each of the spring-loaded mounts 38 interfaces with a respective aperture through the trap door 36 to constrain motion of the trap door 36 relative to the top cover base 24. Each of the spring-loaded mounts 38 also interfaces with a top surface area surrounding the respective aperture to exert a force onto the trap door 36 that presses on the trap door 36 towards the top cover base 24. In the closed configuration illustrated in FIG. 1, the forces exerted by the spring-loaded mounts 38 onto the trap door 36 serves to compress an interface seal disposed between the trap door 36 and the top cover based 24, thereby forming a hermetic seal between the trap door 36 and the top cover base 24.

Reconfiguration of the top cover assembly 14 between the closed configuration and an open configuration will now be described with reference to FIG. 2 through FIG. 6. To reconfigure the top cover assembly 14 to the open configuration, the actuation member 28 is pressed towards the top cover base 24 (i.e., in direction 40). The actuation member 28 is attached to a pivot beam assembly 42, which lifts the trap door 36 away from the top cover base 24 as a result of motion of the actuation member 28 towards the top cover base 24. The pivot beam assembly 42 includes a pair of pivot beams 44, which are pivotally connected with a pivot block 46 for rotation relative to the pivot block 46 about a pivot axis 48. The pivot block 46 is rigidly attached to the top cover base 24. The resulting pivoting of the pivot beams 44 about the pivot axis 48 results in the pivot beams 44 exerting a lifting force on a lifting fitting 50 attached to the trap door 36, thereby lifting the trap door 36 away from the top cover base 24, compressing the springs of the spring-loaded mounts 38, and exposing an opening 52 in the top cover base 24. FIG. 4 shows a side view of the trap door 36 in the closed configuration. FIG. 6 shows a side view of the trap door 36 in the open configuration. And FIG. 5 shows a side view of the trap door 36 in an intermediate configuration between the open and closed configurations.

The latch device 30 is configured to retain the trap door 36 in the open configuration illustrated in FIG. 3 and in FIG. 6 until being disengaged via actuation of the solenoid 32. The latch device 30 includes a latch link 54 and a spring-loaded toggle link 56. The latch link 54 is mounted to the top cover base 24 so as to be constrained to linear translation with no rotation relative to the top cover base 24. A two-force link 58 drivingly connects the actuation member 28 to the latch link 54. In the closed configuration (FIG. 2 and FIG. 4), the two-force link 58 is oriented at an angle relative to a plane normal to the translation direction of the latch link 54. As a result, when the actuation member 28 is pressed towards the top cover base 24, the resulting compression in the two-force link 58 imparts a force component onto the latch link 54 in the translation direction of the latch link 54. The imparted force component causes the latch link 54 to translate from the position of the latch link 54 for the closed configuration of the trap door 36 shown in FIG. 1 and FIG. 2 to the position of the latch link 54 for the open configuration of the trap door shown in FIG. 3. One end of the latch link 54 has a cam surface 60 and a recess 62. The spring-loaded toggle link 56 includes a roller 64 that engages the cam surface 60 when the trap door 36 is in the closed configuration and is received by recess 62 when the trap door 36 is moved to the open configuration. The spring-loaded toggle link 56 is pivotally mounted to the top cover base 24 via a pivot mount 66. A tension spring 68 is connected at one end to the toggle link 56 and at the other end to the top cover base 24, thereby biasing rotation of the toggle link 56 towards contact between the roller 64 and the latch link 54 (e.g., with the cam surface 60 or the recess 62 depending on the position of the trap door 36 relative to the top cover base 24). Translation of the latch link 54 as a result of movement of the actuation member 28 towards the top cover base 24 results in rotation of the toggle link 56 as the roller 64 rolls along the cam surface 60. Further translation of the latch link 54 serves to position the recess 62 to receive the roller 64 via rotation of the toggle link 56 induced by the tension spring 68. Once received within the recess, the toggle link 56 reacts forces applied to the trap door 36 by the spring-loaded mounts 38, thereby retaining the trap door 36 in the open configuration.

The solenoid 32 is configured to controllably rotate the toggle link 56 so as to remove the roller 64 from the recess 62, thereby no longer preventing translation of the latch link 54. Once the latch link 54 is free to translate the forces applied to the trap door 36 by the spring-loaded mounts 38 are no longer reacted into the toggle link 56 via the pivot beam assembly 42, the actuation member 28, the two-force link 58, and the latch link 54; as a result, the trap door 36 transitions from the open configuration to the closed configuration.

Actuation of the solenoid 32 is controlled by the control unit 34. The control unit 34 includes a temperature sensor that is configured to output one or more signals indicative of the temperature inside the interior volume of the apparatus 10 and/or the temperature surrounding the apparatus 10. In many embodiments, the control unit 34 includes control electronics that monitor the temperature sensor output(s) to identify when the measured temperature(s) are equal to or greater than a selected temperature for sterilizing items within the apparatus 10 and to actuate the solenoid 32 after a target period of time (e.g., a duration of time required to sterilize apparatus contents, and optionally an additional duration of time to achieve desirable environmental conditions within the apparatus). Once the target period of time has passed, the control unit 34 actuates the solenoid 32 to reconfigure the apparatus 10 into the closed configuration, thereby disrupting the gas pathway and stopping the flux of gases into or out of the apparatus 10. The apparatus 10 can then be maintained in the closed configuration until the sterilized items within the apparatus 10 are accessed for use. While the sterilization of items described is based on the passing of a target period of time, the point at which the solenoid is actuated can be based on any suitable approach, for example, such as by using the temperature sensor to track the actual temperature profile over time within the interior volume of the apparatus 10 and determining a total sterilization time based on the measured actual temperature profile.

In many embodiments, the control unit 34 includes a pressure sensor that outputs a pressure signal indicative of the internal pressure of the interior volume of the apparatus 10. The control unit 34 can monitor the pressure signal to detect loss of hermetic seal of the apparatus 10. When the apparatus 10 is reconfigured to the closed (hermetically sealed) configuration within a sterilization chamber (e.g., autoclave), the temperature within the interior volume of the apparatus 10 is initially elevated and subsequently cools over time, resulting in a drop in pressure inside the apparatus 10. Without significant entry of air into the apparatus 10, the pressure within the apparatus 10 will typically remain below the surrounding atmospheric pressure. Therefore, the apparatus 10 can include one or more indicators controlled by the control electronics 34 that are used to indicate whether: (1) the interior pressure of the apparatus 10 is below the surrounding atmospheric pressure, thereby indicating retention of the hermetic seal; and (2) the interior pressure of the apparatus is not below the surrounding atmospheric pressure, thereby indicating possible loss of the hermetic seal. For example, a green indicator light (e.g., a green light emitting diode (LED)) can be lit to indicate that the interior pressure of the apparatus 10 is below the surrounding atmospheric pressure. And the green indicator light can be turned off and/or a red indicator light can be lit to indicate that the interior pressure of the apparatus 10 is not below the surrounding atmospheric pressure.

The functionality described above may be achieved by use of electronics such as microcontrollers or hard logic. A microcontroller can be a small computer on a single integrated circuit containing a processor core, memory, and programmable input/output peripherals. Microcontrollers can be designed for embedded applications, in contrast to the microprocessors used in personal computers or other general purpose applications. Microcontrollers can be used in automatically controlled products and devices. By reducing the size and cost compared to a design that uses a separate microprocessor, memory, and input/output devices, microcontrollers make it economical to digitally control many devices and processes. Hard logic can include a combination of electrical components that are operatively connected and designed to perform one or more specific tasks. In contrast, a microcontroller is programmable enabling the ability to perform different tasks by changing the programming code and uploading the programming code to the microcontroller. Sterilization apparatuses described herein can use such electronics to perform related functionality described herein including, but not limited to, reading a continuous signal from a temperature sensor, determining when the sensed temperature is equal to or greater than a predetermined target temperature, initiating a timer, and actuating a solenoid after an elapsed period of time to reconfigure a sterilization apparatus into a closed, hermetically-sealed, configuration.

Figure 7:
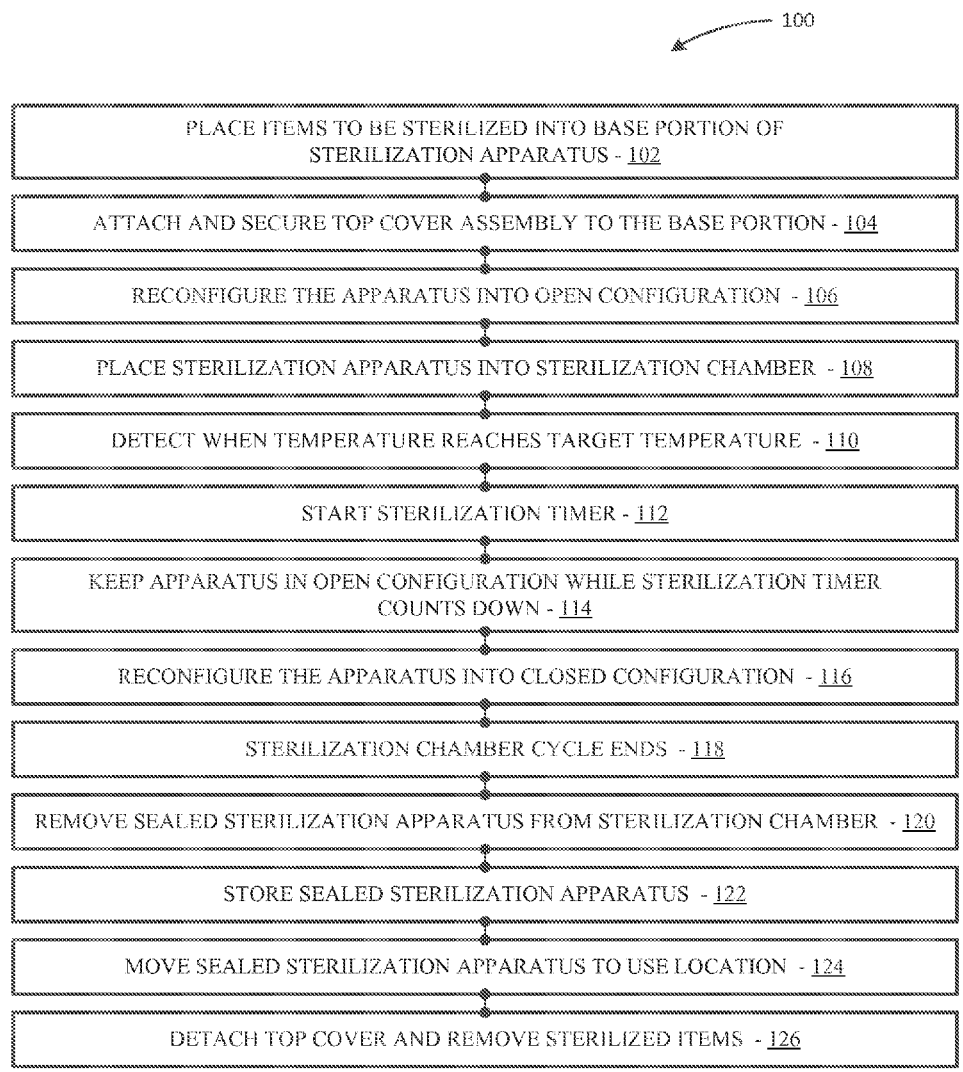
FIG. 7 illustrates acts of a method for sterilizing items and subsequent storage thereof prior to use, in accordance with many embodiments.

FIG. 7 shows acts of a method 100 of sterilizing surgical implements and storing the sterilized surgical instruments prior to use, in accordance with many embodiments. Any suitable sterilization apparatus described herein can be used to accomplish the method 100.

In acts 102 through 106, the sterilization apparatus is prepared for placement into a sterilization chamber. In act 102, items to be sterilized are placed into the base portion of a sterilization apparatus, for example, any of the sterilization apparatus described herein. The items to be sterilized that are placed into the base portion of the sterilization apparatus can include any suitable item, such as, for example, surgical instruments, surgical instrument trays, surgical implants, and/or surgical implant trays. In act 104, the top cover assembly is attached to the base portion and secured. In act 106, the sterilization apparatus is reconfigured to place the trap door into the open configuration.

In acts 108 through 122, a sterilization chamber is used to sterilize the items placed within the sterilization apparatus. In act 108, the sterilization chamber, with the trap door in the open configuration, is placed within a sterilization chamber and the sterilization chamber is turned on, thereby causing the temperature within the sterilization chamber to increase towards a target sterilization temperature or sterilization temperature profile for the sterilization chamber. In act 110, a determination is made that the temperature inside the sterilization apparatus and/or within the sterilization chamber has reached a selected sterilization temperature (e.g., 276 degrees F.). For example, where the sterilization apparatus includes a temperature sensor and an electronic control unit that receives an output of the temperature sensor, the control electronics can monitor the temperature sensor output to determine when the sensed temperature has reached the selected sterilization temperature. As another example, the sterilization apparatus can include a mechanical temperature device, such as a mechanical thermostat, that is used to determine when the sensed temperature has reached the selected sterilization temperature. In act 112, once the selected sterilization temperature is reached, a sterilization timer is started. In act 114, the sterilization timer tracks elapsed time to ensure that the items are subjected to the elevated temperature for a sufficient period of time to sterilize the items. For example, with a selected sterilization temperature of 276 degrees F., the sterilization time period can be set to be greater than or equal to ten minutes. At the end of the sterilization time period, the sterilization apparatus is automatically reconfigured to the closed (hermetically sealed) configuration (act 116). In act 118, the sterilization chamber cycle ends. In act 120, the sealed sterilization apparatus is removed from the sterilization chamber.

The sealed sterilization apparatus can then be stored prior to use of the sterilized items stored within the sterilization apparatus (act 122). When needed, the sterilization apparatus can be brought to a location where the sterilized items are to be removed from the sterilization apparatus (act 124). Once at the use location (e.g., once in a sterile field in an operating room), the top cover assembly of the sterilization apparatus can be removed, thereby breaking the vacuum seal, and the sterilized items removed for use (act 126).

Figure 8:
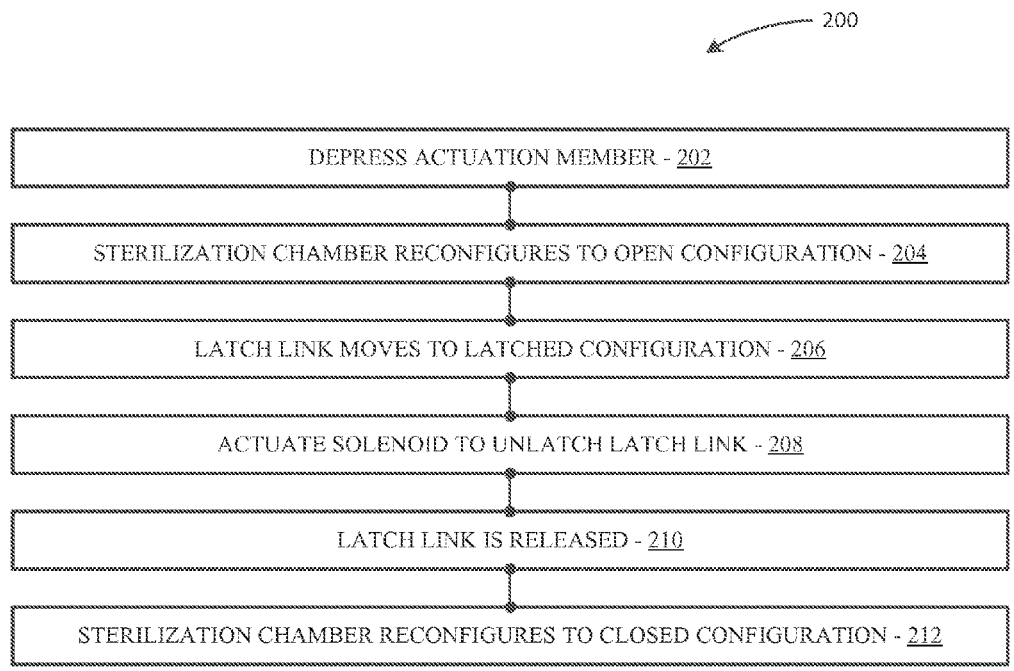
FIG. 8 illustrates acts of a method for reconfiguring an apparatus used to sterilize items and subsequent storage thereof prior to use between open and closed configurations, in accordance with many embodiments.

FIG. 8 shows acts of a method 200 for reconfiguring a sterilization apparatus used to sterilize items and subsequent storage thereof prior to use between open and closed configurations, in accordance with many embodiments. Any suitable sterilization apparatus described herein can be used to accomplish the method 200. The method 200 can be repeated any suitable number of times, for example, to sterilize and store additional items.

In acts 202 through 206, the sterilization apparatus is reconfigured from the closed configuration to the open configuration. In act 202, an actuation member operatively coupled with a trap door is depressed (act 202). As a result, the trap door moves away from the top cover base, thereby opening an air passageway between the interior volume of the sterilization apparatus and the surrounding of the sterilization apparatus (act 204). The movement of the actuation member also produces movement of a latch link to a latched position where it is held in place, thereby serving to hold the trap door in the open configuration (act 206). With the trap door in the open configuration, the sterilization apparatus can be placed into a sterilization chamber and the sterilization chamber turned on.

In acts 208 through 212, the sterilization apparatus is reconfigured from the closed configuration to the open configuration. With the sterilization chamber turned on and heating up, the sterilization apparatus detects when the temperature within the sterilization apparatus and/or within the sterilization chamber reaches a predetermined temperature (e.g., a selected sterilization temperature) and initiates a sterilization timer, which tracks elapsed time to ensure that the items within the sterilization apparatus are subjected to the sterilization temperature for a sufficient period of time to sterilize the items. Once the elapsed time reaches a predetermined time threshold, the latch link is unlatched (e.g., a solenoid is actuated to unlatch the latch link) (act 208). As a result, the latch link is released (act 210). With the latch link released, the sterilization apparatus reconfigures to a closed configuration where the trap door is closed, thereby hermetically sealing the sterilized items within the sterilization apparatus (act 212).

Figure 9:
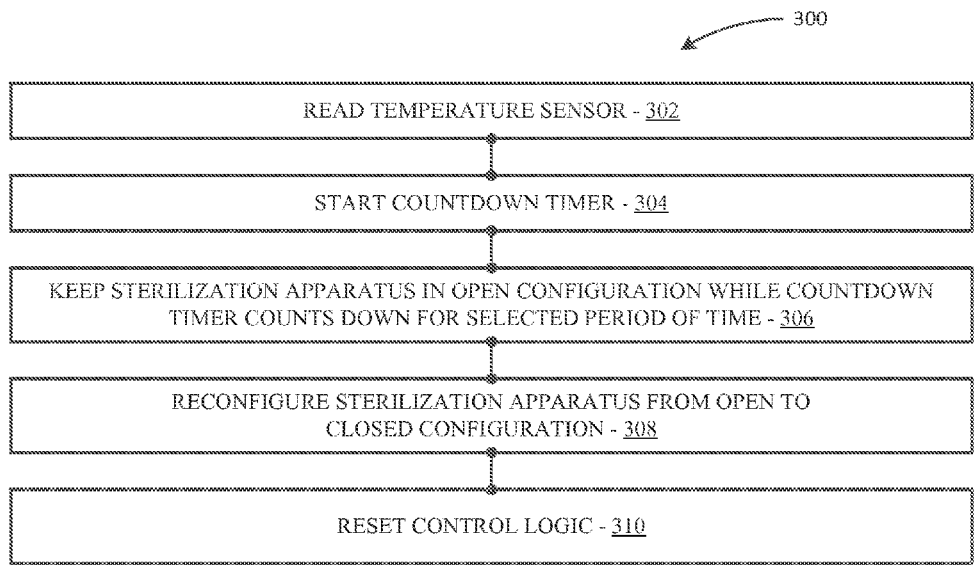
FIG. 9 illustrates acts of a method for controlling a solenoid used to reconfigure an apparatus used to sterilize items and subsequent storage thereof prior to use from an open configuration to a closed configuration following completion of a sterilization of items, in accordance with many embodiments.

FIG. 9 shows acts of a method 300 for controlling a solenoid used to trigger reconfiguration of a sterilization apparatus from an open configuration to a closed configuration, in accordance with many embodiments. The method 300 can be repeated any suitable number of times, for example, as part of a process to sterilize and store additional items.

The method 300 can be accomplished using any suitable sterilization apparatus, for example, using the sterilization apparatus 10 described herein. In act 302, a signal from a temperature sensor is read to determine the current temperature sensed by the temperature sensor (e.g., the temperature inside the sterilization apparatus and/or the temperature within the sterilization chamber). Act 302 is repeated on a regular basis to continually monitor the temperature sensed by the temperature sensor. Once the temperature sensed by the temperature sensor is greater than a predetermined value (e.g., a selected sterilization temperature, for example, 276 degrees F.) a countdown timer is started (e.g., a signal is sent to a countdown timing chip or a microcontroller with a timing chip to commence a countdown of a predetermined time duration) (act 304). The apparatus is kept in the open configuration while the countdown timer counts down for the predetermined time duration, which can be selected to ensure that the items within the sterilization apparatus are subjected to the sterilization temperature for a sufficient period of time to sterilize the items (act 306). For example, the predetermined time duration can be greater than or equal to ten minutes. Once the predetermined time duration has elapsed, a signal is sent to actuate the solenoid so as to reconfigure the sterilization apparatus from the open configuration to the closed configuration (act 308). Upon removal of the sterilization apparatus from the sterilization chamber, the temperature sensed by the temperature sensor reduces. Once the temperature sensed by the temperature sensor reduces below a reset temperature value (e.g., a suitable temperature such as room temperature or a temperature a suitable margin above room temperature), the logic of the control unit accomplishing the method 300 can be reset, thereby preparing the control unit to accomplish another iteration of the method 300.

Figure 10:
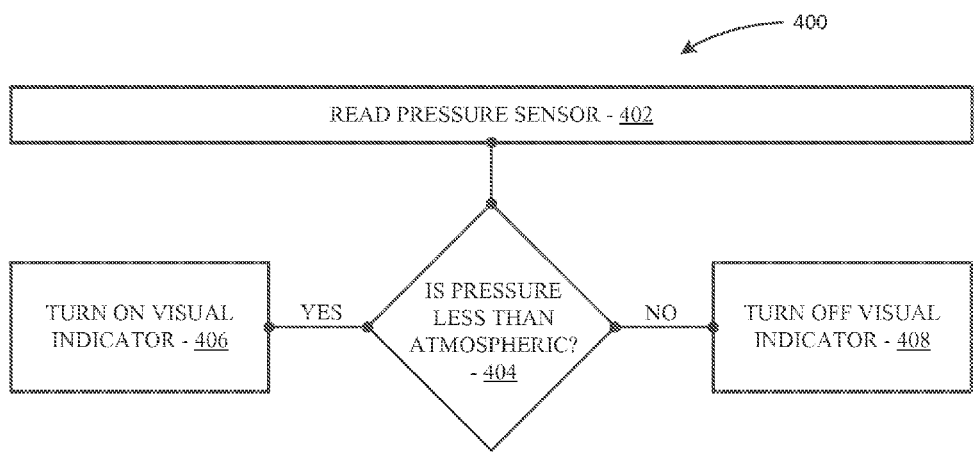
FIG. 10 illustrates acts of a method for monitoring the state of a hermetic sealed internal volume of an apparatus used to sterilize items and subsequent storage thereof prior to use, in accordance with many embodiments.

FIG. 10 shows acts of a method 400 for monitoring the state of seal of a sterilization apparatus used to sterilize and store sterilized items prior to use, in accordance with many embodiments. The method 400 can be repeated any suitable number of times, for example, as part of a process to sterilize and store additional items.

The method 400 can be accomplished using any suitable sterilization apparatus, for example, using the sterilization apparatus 10 described herein. In act 402, a signal from an electronic pressure sensor configured to sense the pressure inside a sterilization apparatus is read and processed to determine the current pressure inside the sterilization apparatus. In many embodiments, a signal from an electronic pressure sensor configured to sense the atmospheric pressure outside the sterilization apparatus is also read and processed to determine the current atmospheric pressure outside the sterilization apparatus. A comparison is made to determine if the current pressure inside the sterilization apparatus is less than atmospheric pressure (act 404). For example, the measured pressure inside the sterilization apparatus can be compared to a measured pressure outside the sterilization apparatus or to a predetermined value for atmospheric pressure. If the pressure inside the sterilization apparatus is less than atmospheric pressure, a visual indicator (e.g., a green light emitting diode (LED)) can be lit (act 406). If the pressure inside the sterilization apparatus is not less than atmospheric pressure, the visual indicator can be turned off. Any suitable indication means can be employed such as, for example, any suitable visual and/or audible indication. The method 400 can be repeated on a regular basis to continually monitor the state of seal of a sterilization apparatus storing sterilized items prior to use.

Figure 11:
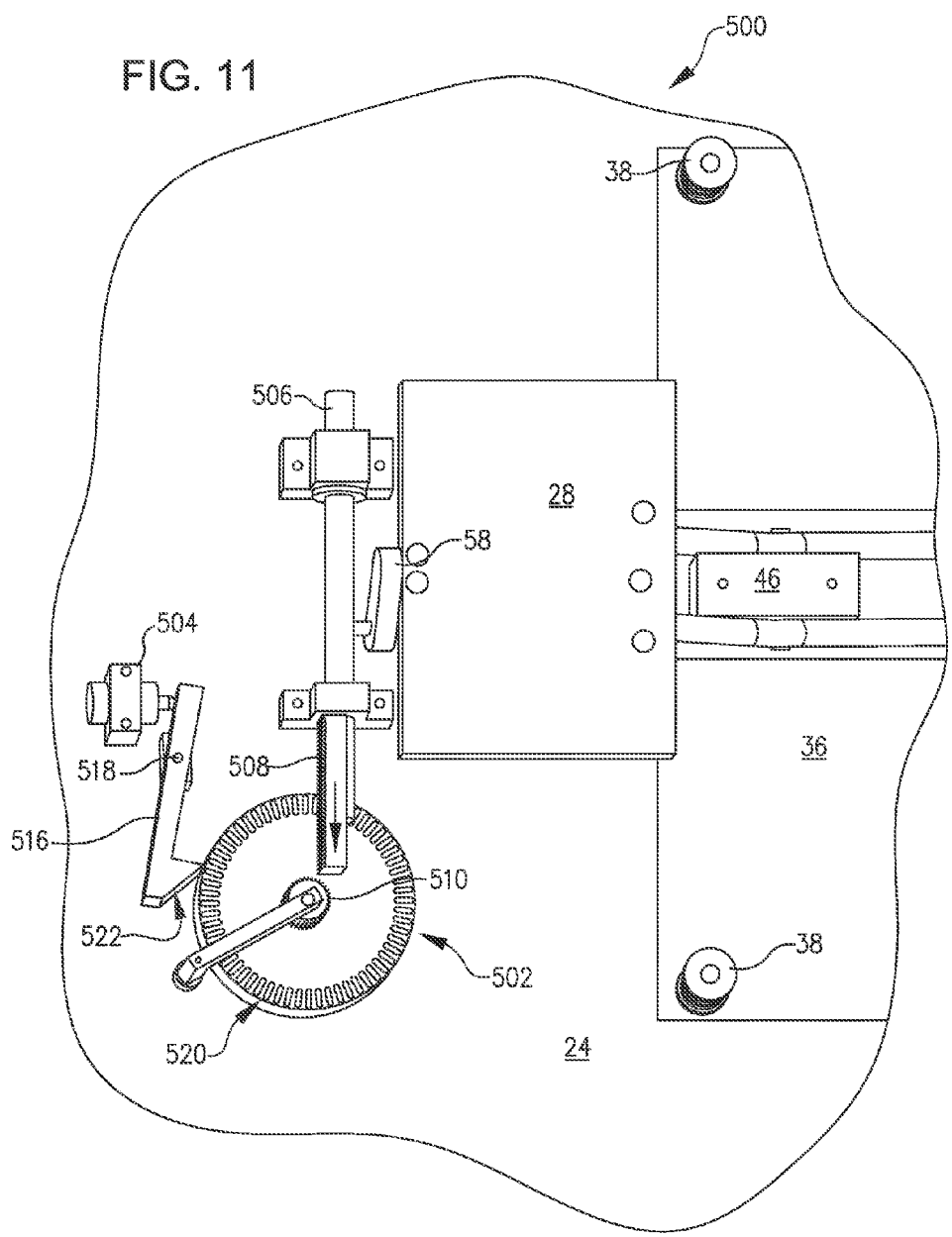
FIGS. 11, 12, and 13 illustrate an actuation sequence of a sterilization and storage apparatus employing a mechanical timer and a mechanical thermostat, in accordance with many embodiments.
Figure 12:
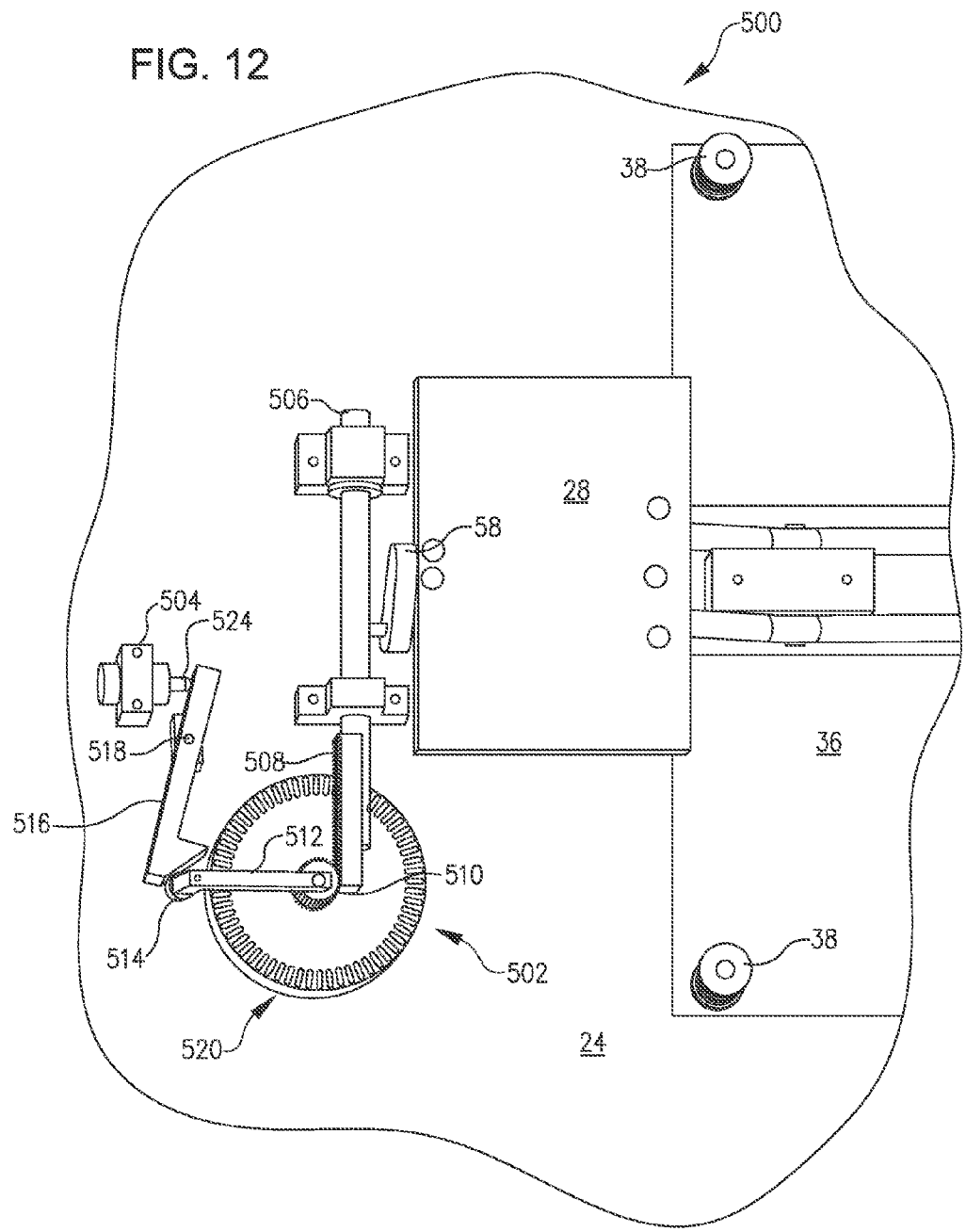
Figure 13:
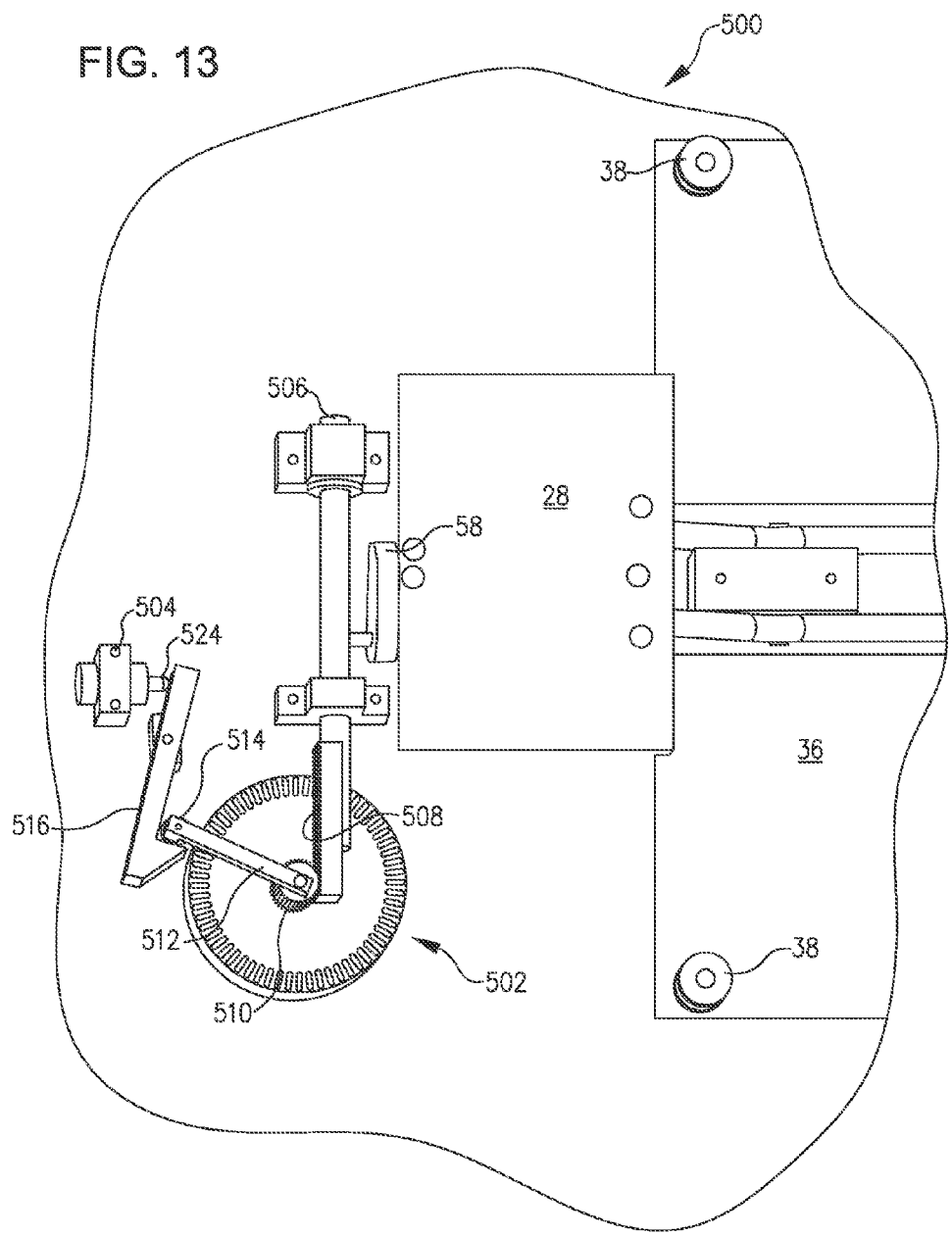

FIGS. 11, 12, and 13 illustrate an actuation sequence of a sterilization and storage apparatus 500 employing a mechanical timer 502 and a mechanical thermostat 504, in accordance with many embodiments. The apparatus 500 is similar to the apparatus 10, but employs a latch mechanism using the mechanical timer 502 and the mechanical thermostat 504. Accordingly, only the components of the apparatus 500 that are different from the corresponding components of the apparatus 10 are described. Any components that are the same are labeled with the same references numbers.

The mechanical timer 502 uses mechanical clockwork to measure time. Analogous manual timers are typically set by turning a dial to the time interval desired; turning the dial stores energy in a mainspring to run the mechanism. The energy in the mainspring causes a balance wheel to rotate back and forth. Each swing of the wheel releases the gear train to move forward by a small fixed amount, causing the dial to move steadily backward until it reaches zero.

FIG. 11 is a partial view of the apparatus 500 in the closed configuration. The apparatus 500 includes a latch link 506. The latch link 506 is mounted to the top cover base 24 so as to be constrained to linear translation with no rotation relative to the top cover base 24. A geared rack 508 is rigidly attached to one end of the latch link 506. The geared rack 508 has gear teeth configured to interface with a pinion gear 510 that is attached to the mechanical timer 502. In the closed configuration illustrated in FIG. 11, the latch link 506 is positioned such that a gap exists between the geared rack 508 and the pinion gear 510.

The two-force link 58 drivingly connects the actuation member 28 to the latch link 506. In the closed configuration (FIG. 11), the two-force link 58 is oriented at a non-zero angle relative to a plane normal to the translation direction of the latch link 506. As a result, when the actuation member 28 is pressed towards the top cover base 24, the resulting compression in the two-force link 58 imparts a force component onto the latch link 506 in the translation direction of the latch link 506. The imparted force component causes the latch link 506 to translate from the position of the latch link 506 for the closed configuration of the trap door 36 shown in FIG. 11 to subsequent positions of the latch link 506 shown in FIG. 12 and FIG. 13.

FIG. 12 shows the apparatus 500 in an intermediate configuration between the closed configuration (FIG. 11) and the open configuration (FIG. 13). From the closed configuration to the intermediate configuration, the motion of the actuation member 28 and the connected two-force link 58 translates the latch link 506 such that the gear rack 508 comes into engagement with the pinion gear 510 and rotates the pinion gear 510, thereby rotating the timer 502. A detent arm 512 is attached to the pinion gear 510 and rotates therewith. A detent roller 514 is rotatably attached to the detent arm 512. In the intermediate configuration illustrated, the translation of the latch link 506 has rotated the pinion gear 510, the timer 502, and the detent arm 512 to an angular orientation in which the detent roller 514 is engaged with a latch member 516.

The latch member 516 is rotatably mounted to the top cover base 24 to rotate about a pivot point 518. In many embodiments, the latch member 516 is mounted to the top cover base 24 so as to rotatably biased toward contact with a perimeter surface 520 of the timer 502. For example, a torsional spring can be connected between the latch member 516 and the top cover base 24 to bias the latch member 516 into contact with the perimeter surface 520. The latch member 516 has a cam surface 522 configured to interface with the detent roller 514 and shaped such that movement of the detent roller 514 in response to movement of the latch link 506 induces rotation of the latch member 516 about the pivot point 518.

Further movement of the actuation member 28 towards the top cover base 24 is used to reconfigure the apparatus 500 from the intermediate configuration illustrated in FIG. 12 to the open and latched configuration illustrated in FIG. 13. The further movement of the actuation member 28 induces a corresponding further translation of the latch link 506; which induces a corresponding additional rotation of the mechanical timer 502, the pinion 510, and detent arm 512; which induces a corresponding additional movement of the detent roller 514, which induces rotation of the detent arm 516 via engagement of the cam surface 520 with the detent roller 514. After the detent roller 514 moves beyond the cam surface 520, the detent arm 516 rotates to capture the detent roller 514 as illustrated in FIG. 13. After the detent roller 514 is captured by the detent arm 516, the actuation member 28 can be released and the apparatus 500 will remain in the open configuration until unlatched via the action of the detent arm 516 and react the forces applied by the spring-loaded mounts 38 via the interconnecting linkage.

The apparatus 500, in the open configuration illustrated in FIG. 13, can then be placed into a sterilization chamber and the sterilization chamber turned on. The resulting increase in temperature induces a configuration change to the mechanical thermostat 504. The mechanical thermostat 504 is configured to extend a plunger 524 towards the detent arm 516 in response to increased temperature so as to rotate the detent arm 516 out of engagement with the detent roller 514 at a desired temperature level (e.g., at a selected sterilization temperature, for example, 276 degrees F.). When the detent roller 514 is no longer constrained by the detent arm 516, the mechanical timer 502 begins to operate and slowly rotate from the angular orientation shown in FIG. 13 to the angular orientation shown in FIG. 12 and finally to an angular rotation in which the geared rack 508 becomes disconnected from the pinion gear 510, thereby releasing the trap door 36 to the closed configuration and sealing the sterilized items within the apparatus 500.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An apparatus for sterilizing surgical implements within a sterilization chamber and storing the sterilized surgical implements prior to use, the apparatus comprising:

a container configured to receive one or more surgical implements, the container comprising a base portion and a top cover selectively attachable to and detachable from the base portion;

a trap door coupled with the container so as to be reconfigurable between a closed configuration in which the trap door and the container at least partially define an internal volume that is hermetically sealed and an open configuration in which the trap door is displaced from the container to form a fluid passage between the internal volume and a volume within the sterilization chamber and external to the container, the top cover of the container having an opening that is blocked by the trap door when the trap door is in the closed configuration, the opening not being blocked by the trap door when the trap door is in the open configuration;

a mechanism operatively coupled with the trap door and the container, the mechanism being configured for selective reconfiguration of the trap door from the closed configuration to the open configuration and to automatically reconfigure the trap door from the open configuration to the closed configuration after completion of a sterilization of one or more surgical implements disposed within the internal volume; and one or more spring elements that: (a) generate an interface force between the trap door and the top cover when the trap door is in the closed configuration; and (b) generate a force on the trap door that is reacted by the mechanism when the trap door is in the open configuration;

wherein the mechanism comprises:

an actuation member that a user manually displaces to reconfigure the trap door from the closed configuration to the open configuration;

a latch device that maintains the trap door in the open configuration until after the completion of the sterilization;

a temperature sensor configured to generate a temperature sensor output indicative of a temperature of the internal volume;

a solenoid coupled with the latch device and operable to unlatch the latch device so as to cause reconfiguration of the trap door from the open configuration to the closed configuration; and a control unit receiving the temperature sensor output and controlling the solenoid, the control unit determining completion of the sterilization and actuating the solenoid after the completion of the sterilization to unlatch the latch device.

2. The apparatus of claim 1, wherein the control unit determines completion of the sterilization based on the temperature of the internal volume being equal to or greater than a selected sterilization temperature for a period of time.

3. The apparatus of claim 1, wherein the control unit delays actuation of the solenoid for a period of time after completion of the sterilization.

4. The apparatus of claim 1, wherein the latch device comprises a rotatable link that is rotatable by the solenoid from a latched orientation that maintains the trap door in the open configuration to an unlatched orientation that permits reconfiguration of the trap door from the open configuration to the closed configuration.

5. The apparatus of claim 1, wherein:
the trap door comprises a plurality of apertures, each of the apertures being configured to receive and interface with a respective guide feature attached to the container so as to constrain movement of the trap door relative to the container between the closed configuration and the open configuration;
the actuation member is coupled with the trap door via a beam member mounted to rotate about a pivot point that is fixed relative to the container; and
the actuation member is coupled with the latch device via a two-force link that is oriented transverse to a movement direction of the actuation member relative to the container for each of the open and closed configurations of the trap door.

6. The apparatus of claim 5, wherein the latch device comprises a latch link constrained to linear translation relative to the container, the latch link being drivable via the two-force link between a latched position used to hold the trap door in the open configuration and a position for which the trap door is in the closed configuration.

7. The apparatus of claim 6, wherein the latch link has a cam surface and a recess, wherein movement of the latch link toward the latched position engages a spring-biased latch member with the cam surface to position the latch member for engagement with the recess.

8. The apparatus of claim 7, wherein actuation of the solenoid drives the spring-biased latch member out of engagement with the recess, thereby permitting movement of the latch link from the latched position to the position for which the trap door is in the closed configuration.

9. The apparatus of claim 1, wherein the latch device is operatively coupled with the trap door via a linkage that reacts the force generated on the trap door by the one or more spring elements into the latch device when the trap door is in the open configuration.

10. An apparatus for sterilizing surgical implements within a sterilization chamber and storing the sterilized surgical implements prior to use, the apparatus comprising:
a container configured to receive one or more surgical implements, the container comprising a base portion and a top cover selectively attachable to and detachable from the base portion;
a trap door coupled with the container so as to be reconfigurable between a closed configuration in which the trap door and the container at least partially define an internal volume that is hermetically sealed and an open configuration in which the trap door is displaced from the container to form a fluid passage between the internal volume and a volume within the sterilization chamber and external to the container, the top cover of the container having an opening that is blocked by the trap door when the trap door is in the closed configuration, the opening not being blocked by the trap door when the trap door is in the open configuration;
a mechanism operatively coupled with the trap door and the container, the mechanism being configured for selective reconfiguration of the trap door from the closed configuration to the open configuration and to automatically reconfigure the trap door from the open configuration to the closed configuration after completion of a sterilization of one or more surgical implements disposed within the internal volume; and
one or more spring elements that: (a) generate an interface force between the trap door and the top cover when the trap door is in the closed configuration; and (b) generate a force on the trap door that is reacted by the mechanism when the trap door is in the open configuration;
wherein the mechanism comprises:
an actuation member that a user manually displaces to reconfigure the trap door from the closed configuration to the open configuration;
a latch device that maintains the trap door in the open configuration until after the completion of the sterilization;
a mechanical thermostat having a first configuration at a first temperature below a sterilization temperature and having a second configuration at a second temperature equal to or greater than the sterilization temperature; and
a mechanical timer,
the latch device being operatively coupled with the mechanical thermostat and configured to block a timing operation of the mechanical timer when the mechanical thermostat is in the first configuration and permit the timing operation when the thermostat is in the second configuration, and
the mechanical timer being coupled with the trap door via a linkage so as to maintain the trap door displaced from the container until expiration of a time period determined by the mechanical timer.

11. The apparatus of claim 10, wherein a user displacement of the actuation member translates a geared rack to engage and rotate a timer gear drivingly coupled with the mechanical timer so as to wind the mechanical timer to enable the mechanical timer to effect the timing operation.

12. The apparatus of claim 11, wherein the geared rack becomes disengaged from the timer gear to permit reconfiguration of the trap door into the closed configuration.

* * * * *